(12) United States Patent
Sevrain (10) Patent No.: US 9,084,646 B2
(45) Date of Patent: Jul. 21, 2015

(54) UNIVERSAL ANCHOR FOR ATTACHING OBJECTS TO BONE TISSUE

(75) Inventor: Lionel C. Sevrain, West Palm Beach, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 86 days.

(21) Appl. No.: 12/934,196

(22) PCT Filed: Mar. 26, 2009

(86) PCT No.: PCT/US2009/038376
§ 371 (c)(1),
(2), (4) Date: Sep. 23, 2010

(87) PCT Pub. No.: WO2009/120852
PCT Pub. Date: Oct. 1, 2009

(65) Prior Publication Data
US 2011/0022066 A1    Jan. 27, 2011

Related U.S. Application Data

(60) Provisional application No. 61/039,464, filed on Mar. 26, 2008.

(51) Int. Cl.
*A61B 17/04* (2006.01)
*A61B 17/86* (2006.01)
*A61F 2/08* (2006.01)
*A61B 17/88* (2006.01)

(52) U.S. Cl.
CPC ............. *A61B 17/86* (2013.01); *A61B 17/8685* (2013.01); *A61B 17/8875* (2013.01)

(58) Field of Classification Search
USPC .................................................. 606/300–321
See application file for complete search history.

(56) References Cited

U.S. PATENT DOCUMENTS

| 928,997 A | 7/1909 | Muller |
| 3,474,537 A | 10/1969 | Christensen |

(Continued)

FOREIGN PATENT DOCUMENTS

| CN | 1665459 | 9/2005 |
| CN | 101094618 | 12/2007 |

(Continued)

OTHER PUBLICATIONS

Rajasekaran et al., "Translaminar Facetal Screw (Magerl's) Fixation", Neurology India, Dec. 2005, 53(4), 5 pages.

*Primary Examiner* — Andrew Yang
*Assistant Examiner* — Diana S Jones
(74) *Attorney, Agent, or Firm* — Baker & Hostetler LLP (57) ABSTRACT

An anchoring device and method for attaching an object to a bone comprises an anchoring member having proximal and distal ends, with the proximal end being adapted to hold the object to the bone while the distal end is in the bone, and a locking member having proximal and distal ends, with the proximal end adapted to secure the anchoring member into the bone and oppose its pull-out or loosening by stopping its backing or preventing its unscrewing while the distal end is in the bone. Also provided are first and second fasteners, with the first fastener adapted to fit to the proximal end of the anchoring member, and the second fastener adapted to fit to the proximal end of the locking member. The end of the second fastener can have an angle that matches an angle of the locking member.

43 Claims, 10 Drawing Sheets

(56) References Cited

U.S. PATENT DOCUMENTS

| | | | |
|---|---|---|---|
| 4,338,835 A | 7/1982 | Simons | |
| 4,759,766 A | 7/1988 | Buettner-Janz et al. | |
| 5,038,978 A | 8/1991 | Kolton et al. | |
| 5,140,877 A * | 8/1992 | Sloan | 81/439 |
| 5,207,529 A | 5/1993 | Bailey | |
| 5,251,521 A | 10/1993 | Burda et al. | |
| 5,425,767 A | 6/1995 | Steininger et al. | |
| 5,443,469 A | 8/1995 | Smith | |
| 5,505,731 A | 4/1996 | Tornier | |
| 5,797,918 A * | 8/1998 | McGuire et al. | 606/104 |
| 5,899,941 A | 5/1999 | Nishijima et al. | |
| 5,984,681 A * | 11/1999 | Huang | 433/174 |
| 5,993,463 A | 11/1999 | Truwit | |
| 6,013,078 A | 1/2000 | Lin | |
| 6,113,637 A | 9/2000 | Gill et al. | |
| 6,168,598 B1 | 1/2001 | Martello | |
| 6,270,499 B1 | 8/2001 | Leu et al. | |
| 6,467,919 B1 | 10/2002 | Rumsey et al. | |
| 6,648,892 B2 | 11/2003 | Martello | |
| 6,695,844 B2 | 2/2004 | Bramlet et al. | |
| 6,849,093 B2 | 2/2005 | Michelson | |
| 7,004,629 B2 | 2/2006 | Shrader | |
| 7,094,242 B2 | 8/2006 | Ralph et al. | |
| 7,163,540 B2 | 1/2007 | Martello | |
| 7,198,643 B2 | 4/2007 | Zubock et al. | |
| 7,198,644 B2 | 4/2007 | Schultz et al. | |
| 7,326,248 B2 | 2/2008 | Michelson | |
| 7,524,326 B2 | 4/2009 | Dierks | |
| 7,597,713 B2 | 10/2009 | Baumgartner et al. | |
| 7,883,513 B2 | 2/2011 | Ralph et al. | |
| 7,887,590 B2 | 2/2011 | Levieux | |
| 7,981,114 B2 | 7/2011 | Zander | |
| 8,361,157 B2 | 1/2013 | Bouttens et al. | |
| 2002/0128712 A1 * | 9/2002 | Michelson | 623/17.11 |
| 2003/0135216 A1 | 7/2003 | Sevrain | |
| 2003/0171753 A1 | 9/2003 | Collins et al. | |
| 2003/0199876 A1 | 10/2003 | Brace et al. | |
| 2004/0111161 A1 | 6/2004 | Trieu | |
| 2005/0018931 A1 | 1/2005 | Shrader et al. | |
| 2005/0033438 A1 | 2/2005 | Schultz et al. | |
| 2005/0107791 A1 * | 5/2005 | Manderson | 606/62 |
| 2006/0052787 A1 | 3/2006 | Re et al. | |
| 2006/0064095 A1 | 3/2006 | Senn et al. | |
| 2006/0116676 A1 | 6/2006 | Gradel et al. | |
| 2006/0189991 A1 * | 8/2006 | Bickley | 606/72 |
| 2007/0112354 A1 | 5/2007 | Iwasaki et al. | |
| 2007/0191952 A1 | 8/2007 | Bernero | |
| 2007/0213729 A1 | 9/2007 | Lindemann et al. | |
| 2008/0140130 A1 | 6/2008 | Chan et al. | |
| 2008/0221623 A1 | 9/2008 | Gooch | |
| 2008/0221624 A1 | 9/2008 | Gooch | |
| 2008/0243253 A1 | 10/2008 | Levieux | |
| 2009/0120852 A1 | 5/2009 | Ellsworth et al. | |
| 2009/0326545 A1 | 12/2009 | Schaffhausen | |
| 2010/0121324 A1 | 5/2010 | Tyber et al. | |
| 2010/0121325 A1 | 5/2010 | Tyber et al. | |
| 2010/0145397 A1 | 6/2010 | Overes et al. | |
| 2010/0160924 A1 | 6/2010 | Soliman | |
| 2010/0167240 A1 | 7/2010 | Benzon et al. | |
| 2010/0256638 A1 | 10/2010 | Tyber et al. | |
| 2010/0256639 A1 | 10/2010 | Tyber et al. | |
| 2010/0312280 A1 | 12/2010 | Overes et al. | |
| 2010/0324556 A1 | 12/2010 | Tyber et al. | |
| 2011/0022066 A1 | 1/2011 | Sevrain | |
| 2011/0118739 A1 | 5/2011 | Tyber et al. | |
| 2011/0125153 A1 | 5/2011 | Tyber et al. | |
| 2011/0137312 A1 | 6/2011 | Mantovani et al. | |
| 2011/0160729 A1 | 6/2011 | Overes et al. | |
| 2011/0184470 A1 | 7/2011 | Gorek et al. | |
| 2011/0213367 A1 | 9/2011 | Tyber et al. | |
| 2011/0230884 A1 | 9/2011 | Mantzaris et al. | |
| 2011/0230920 A1 | 9/2011 | Gorek et al. | |
| 2011/0282398 A1 | 11/2011 | Overes et al. | |

FOREIGN PATENT DOCUMENTS

| | | |
|---|---|---|
| CN | 101102730 | 1/2008 |
| CN | 10229043 | 12/2011 |
| EP | 0330328 | 8/1989 |
| EP | 1658816 | 5/2006 |
| EP | 1779794 A1 | 5/2007 |
| JP | 54-118566 | 8/1979 |
| JP | 2001-252283 | 9/2001 |
| JP | 2001-520071 A | 10/2001 |
| JP | 2003-518408 | 10/2003 |
| JP | 2006-514238 | 4/2006 |
| KR | 10-2011-7015221 | 12/2009 |
| WO | WO 99/47061 A1 | 9/1999 |
| WO | WO 00/38586 A1 | 7/2000 |
| WO | WO 00/69352 | 11/2000 |
| WO | WO 2006/016384 | 2/2006 |
| WO | WO 2006/119092 | 11/2006 |
| WO | WO 2007/048038 A2 | 4/2007 |
| WO | WO 2007/098288 | 8/2007 |
| WO | WO 2009/092907 | 7/2009 |
| WO | WO 2009/149371 | 12/2009 |
| WO | WO 2010/065855 | 6/2010 |
| WO | WO 2011/155931 | 12/2011 |

* cited by examiner

UNIVERSAL ANCHOR FOR ATTACHING OBJECTS TO BONE TISSUE

CROSS-REFERENCE TO RELATED APPLICATIONS

This application is the National Stage of International Application No. PCT/US2009/038376, filed Mar. 26, 2009, which claims the benefit of U.S. Provisional Application No. 61/039,464, filed Mar. 26, 2008, the disclosures of which are incorporated herein by reference in their entireties for all purposes.

FIELD OF THE INVENTION

The present invention relates to devices for attaching various objects, such as prostheses or implants, to bones, and in certain cases for anchoring spinal instruments to the vertebrae of the human rachis.

BACKGROUND OF THE INVENTION

The fast-growing aging population represents an important orthopedic market with a very specific need related to its low-quality cancelous or spongy bone (osteoporosis). Osteosynthesis procedures in such people are jeopardized by the risk of loosening in relation with the pullout or back-out of anchors in the bone. The reliability of an anchoring system depends on its ability to resist pulling out of the bone. Removal of an anchor may lead to extrusion, or even worse, loosening of any object attached to the bone. Known anchoring systems propose several solutions: Divergent or convergent screws have been proposed to oppose to pull out forces by increasing the grip. Locking mechanisms intended to secure the anchor within the object (such as locking screw or anti-reverse systems) avoid the pull out of the anchor but not the extrusion of the entire construct. Bicortical screwing may be dangerous and can make the construct too rigid. This can lead to the breakage of the implant itself. Special features like conical core, self-tapping profile and roughened surfaces of the anchor have been developed to increase the grip to the cancelous bone. Expandable mechanisms (such as threaded peg expanded with a coaxial inner member or "Molly screw") crush and split fragile bone tissue and then creates an empty room around the buried part of the anchor. This can lead the construct to toggle and therefore to a condition for pull out or loosening in response to physiological micro-motions.

U.S. Pat. No. 6,695,844 to Bramlet et al discloses an expandable-winged fastener made up of an outer member and an inner mechanism able to protract or retract wings intended not only to increase the interface between the bone and the device but also to expand within the cancelous bone. Although the wings are blunted, the bone-implant interface is weakened as the wings expand or retract because the expanded wings broach through the bone as they pivot and therefore require the bone to remodel.

Other solutions use an interlocking mechanism, such as a K-wire which intersect a bone screw ("An Interlocking Screw for Fixation in Osteoporotic Bone" described by McKoy and al. in "internal fixation in osteoporotic bone" authored by Yuehuei H. An in 2002) or two members connected by their ends through a threaded connection ("Anchoring System for Fixing Object to bones" U.S. patent application Ser. No. 10/275,710 to Lionel Sevrain).

Connecting solutions address some of the problems, and provide increased strength and reliability, but require an aiming system that may represent a hurdle not only from a marketing standpoint but also from an anatomical standpoint. There is therefore a need for an improved anchoring system and installation method for anchoring an object to bone.

It would be desirable to provide a novel anchoring system for securing various objects to bones, such as spinal devices or instrumentations to the rachis, and to provide an anchoring system well adapted to prevent a pull out of the anchor and therefore the extrusion and/or the loosening of the object over time. It would also be desirable to provide an anchoring system to bring the needed reliability in such osteoporotic bone, without the hassle of an additional aiming guide.

SUMMARY OF THE INVENTION

Therefore, in accordance with a first aspect, there is provided an anchoring device for attaching an object to a bone, comprising an anchoring member having proximal and distal ends, the proximal end being adapted to hold the object to the bone while the distal end is in the bone, and a locking member having proximal and distal ends, with the proximal end adapted to secure the anchoring member into the bone and oppose its pull-out or loosening by stopping its backing or preventing its unscrewing, while the distal end is in the bone.

Also in accordance with another aspect, there is provided first and second fasteners, the first fastener being adapted to fit to the proximal end of the anchoring member, and the second fastener being adapted to fit to the proximal end of the locking member. More specifically, the second fastener is adequately designed to match the angulation of the locking member.

Further in accordance with another aspect, there is provided a method for mounting an object to a bone, comprising the steps of: (a) providing anchoring member and locking member each having proximal and distal ends, (b) introducing the anchoring member in the bone wherein said proximal end holds an object to the bone, (c) positioning the locking member into the proximal end of the anchoring member, and (d) preventing the anchoring member of loosening.

In one embodiment of the invention, there is a system for attaching one or more objects to bone tissue, comprising: an anchoring member having proximal and distal ends, wherein the proximal end comprises a socket and an aperture, wherein the aperture is oblique to the axis of the length of the anchoring member; and a locking member having proximal and distal ends, wherein the proximal end comprises a socket; wherein the aperture of the anchoring member is adapted for insertion of the locking member therethrough. In a specific embodiment, the system further comprises at least one fastener, wherein the fastener is adapted to fit to a socket in the proximal end of the anchoring member, adapted to fit to a socket in the proximal end of the locking member, or both. In one specific embodiment, the system further comprises first and second fasteners, wherein the first fastener is adapted to fit to a socket in the proximal end of the anchoring member and the second fastener is adapted to fit to a socket in the proximal end of the locking member.

In another embodiment of the invention, the angle on the head of the second fastener corresponds to the angulation of the locking member inserted into the anchoring member. In other specific embodiments, the anchoring member, the locking member, or both have a rough surface. In certain aspects, the surface of the inner wall of the aperture is smooth, rough, or threaded. In particular aspects of the invention, the angle between the axis of the length of the anchoring member and the axis of the length of the locking member is between 1 and 89 degrees, between 10 and 75 degrees, between 10 and 50 degrees, between 10 and 35 degrees, or between 25 and 30 degrees.

In a specific embodiment of the invention, the shape of the socket of the anchoring member and/or the shape of the socket of the locking member is hexagonal, pentagonal, square, triangular, cross-shaped, plus sign-shaped, linear, or star-shaped. In a particular aspects of the invention, the second fastener is a ball end hexagonal fastener.

In one embodiment of the invention, there is a method of affixing one or more objects to bone, comprising the step of anchoring the object to the bone using the system(s) or composition(s) of the invention. In another embodiment of the invention, there is a kit comprising the system(s) or composition(s) of the invention.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Having thus generally described the nature of the invention, reference will now be made to the accompanying drawings, showing by way of illustration a particular embodiment thereof.

From the foregoing disclosure and the following more detailed description of various particular embodiments it will be apparent to those skilled in the art that the present invention provides a significant advance in the art of bone anchoring devices. Additional features and advantages of various particular embodiments will be better understood in view of the detailed description provided below.

DETAILED DESCRIPTION OF THE INVENTION

The present invention incorporates by reference herein in its entirety U.S. Provisional Patent Application Ser. No. 60/896,960, filed Mar. 26, 2007.

The term "a" or "an" as used herein in the specification may mean one or more. As used herein in the claim(s), when used in conjunction with the word "comprising", the words "a" or "an" may mean one or more than one. As used herein "another" may mean at least a second or more. Some embodiments of the invention may consist of or consist essentially of one or more elements, method steps, methods and/or systems of the invention. It is contemplated that any system, method, or composition described herein can be implemented with respect to any other method or composition described herein.

I. The Present Invention

It will be apparent to those skilled in the art, that is, to those who have knowledge or experience in this area of technology, that many variations are possible for the system for anchoring bone disclosed herein. The following detailed discussion of various and particular features and embodiments will illustrate the general principles of the invention with reference to an improved bone anchoring device for use in mammalian bone, including vertebrae, for example. Other embodiments suitable for other applications will be apparent to those skilled in the art given the benefit of this disclosure.

Any mammalian bone, including human bone, may have the inventive systems, methods, and/or compositions of the present invention applied thereto. Examples include long, short, flat, irregular, accessory, and sesamoid bones. Particular examples include but are not limited to vertebrae, femur, humerus, radius, ulna, femur, tibia, fibula, clavicle, rib, metacarpals, metatarsals, phalanges, skull bones, sternum, scapulae, innominates, vertebrae, maxillae, sphenoid, carpus, tarsus, patella, interfrontal bone, epipteric bone, coronal ossicle, bregmatic ossicle, sagittal ossicle, lambdoid ossicle, and squame-parietal ossicle.

The materials of the components of the present invention may be of any suitable kind. Materials of the anchor and locking member are biocompatible, in certain embodiments. Examples of materials include biomedical metallic materials, including stainless steel; alloys (Al, Co, Ni, Ta, W, V, etc.);

cobalt-based alloys; or titanium and its alloys. Other examples of materials include polymeric biomaterials, such as synthetic non-biodegradable polymers: polyethylene (high density polyethylene—HDPE—, ultrahigh molecular weight polyethylene—UHMWPE—), poly (ether ether ketone) or PEEK. Polymer matrix composite biomaterials may be employed and include fiber-reinforced composites (for example, carbon fiber or kevelar).

The shape, diameter, length, and any associated angles of the anchor, locking member, and, by extrapolation, fastener(s) of the invention maybe of any kind, so long as the locking member is able to be positioned within the anchor at an angle to generate a V-shaped (or L-shaped, in a 90 degree configuration) configuration and so long as the corresponding fastener(s) can be inserted in the respective socket 104 in the head of anchor and/or locking member to apply torque for affixing them into bone.

Referring now to FIGS. 1 to 9, in accordance with an illustrative embodiment of the present invention, an anchoring device or implant, generally referred to using the numeral 100, will now be described. The anchoring system 100 is generally comprised of an anchoring member A and a locking member L (see FIG. 3)

Figure 1:
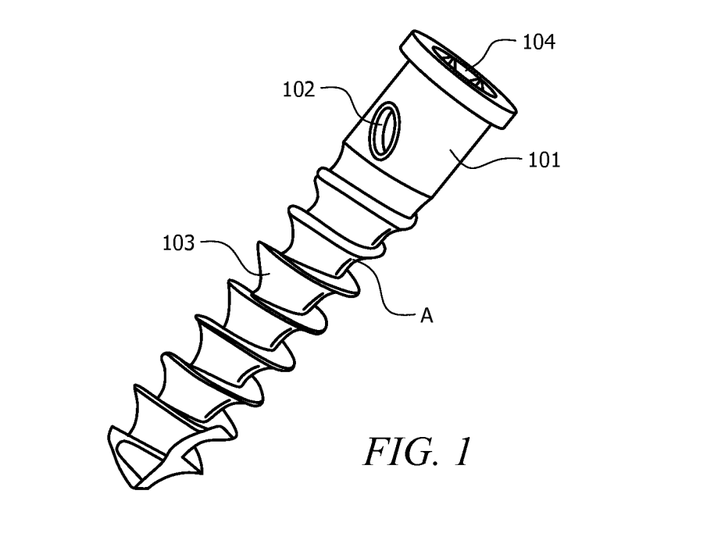
FIG. 1 is a schematic perspective view of an anchoring member in accordance with the present invention.

FIG. 1 illustrates an anchoring member A in accordance with a certain embodiment. The anchoring member A generally has cancelous screws' features such as a 2-portion shaft comprising an optionally coarse, self-tapping thread 103, designed to anchor in the softer medullary or cancelous bone, and topped by a smooth unthreaded portion 101 that allows it to act as a lag screw. The unthreaded upper portion 101 presents an oblique aperture 102 having an angle (for example, of about)25° with respect to an axial plane of the anchoring member's shaft. The proximal end of the anchoring member A has a proximal end socket 104 such that it can be engaged by a fastener like a key, screwdriver, or wrench (see FIG. 2b). In specific embodiments, the proximal end of the anchoring member A has a Hex (hexagonal) type's proximal end socket 104 such that it can be engaged by a Hex tip fastener like a key or wrench (see FIG. 2b).

The term "fastener" as used herein refers to a tool, such as a wrench, key, or screwdriver, that is employed to insert the corresponding anchor in the bone via the head of the anchor and/or to insert the corresponding locking member in the anchor via the socket 104 of the head of the locking member.

Although the socket 104 of the head of the anchor or locking member may be of any shape, the embodiment presented herein wherein both heads are hexagonal is merely illustrative. That is, the shape of the socket 104 for insertion of the respective fastener in the anchor or locking member may be of any shape, including hexagonal, pentagonal, square, triangular, cross-shaped, plus sign-shaped, linear, star-shaped, and so forth, for example. In a specific embodiment, the head of the locking member is smaller than the head of the anchor, although in other embodiments the head of the locking member is the same size as the head of the anchor. In another specific embodiment, the socket 104 of the proximal end of the anchor and the socket 104 of the proximal end of the locking member are identical in shape and/or size, whereas in other specific embodiments the socket 104 of the proximal end of the anchor and the socket 104 of the proximal end of the locking member are not identical in shape and/or size.

Figure 2A:
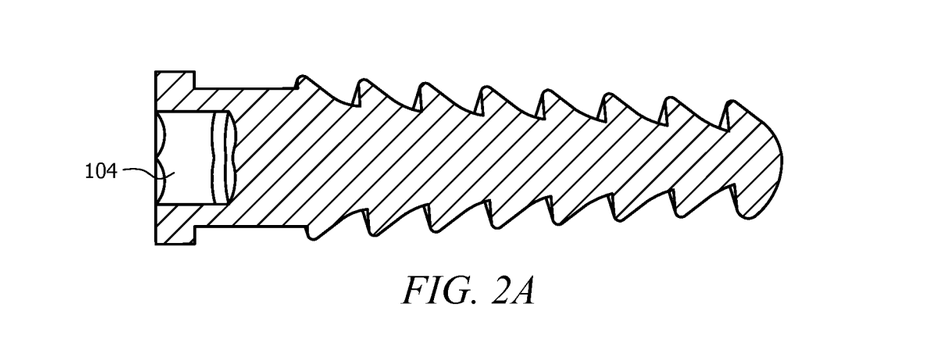
FIG. 2*a* is a schematic cross-sectional plan view of an anchoring member.
Figure 2B:
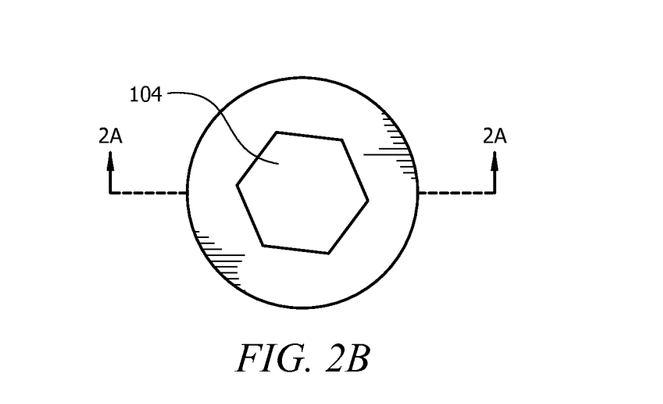
FIG. 2*b* is a top plan schematic view of the proximal end of the anchoring member.

FIG. 2 shows a cross-sectional view of the anchoring member (FIG. 2a) and a top plan of the proximal end of the anchoring member (FIG. 2b). The shape of the socket 104 for insertion of the respective fastener in the anchor or locking member may be of any shape, including hexagonal, pentagonal, square, triangular, cross-shaped, plus sign-shaped, linear, star-shaped, and so forth, for example (see below); these may be referred to as slotted, Phillips, Pozidriv, torx, Hex key, Robertson, Tri-Wing, Torq-Set, or Spanner, for example.

However, an exemplary hexagonal (Hex) socket in the head (104) of the anchoring member brings the following advantage: a ball end hex key (or wrench) can be used for angulated screwing and insertion, the contact surfaces of the screw are protected from external damage, the tool can be used with a headless screw, there are six contact surfaces between screw and driver, the socket's depth are less prone to stripping, and this room can be used for cannulation, for example.

Figure 3:
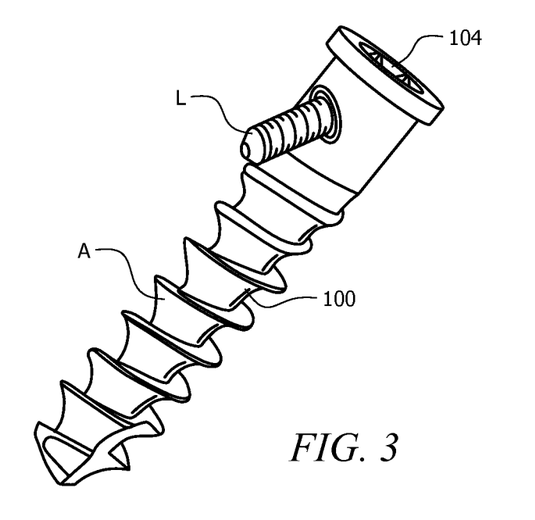
FIG. 3 is a schematic perspective view of an anchoring member with the locking member.

FIG. 3 illustrates the anchoring system 100 comprising the anchoring member A and the locking member L. The angle α between the two members is fixed and set up at 25 degrees in a certain embodiment. This angle allows using a standard hex second fastener F2 (wherein F1 fastener refers to the fastener for the anchor and F2 fastener refers to the fastener for the locking member) equipped with an end ball hex end since it can be used with an angulation up to 30 degrees. In other embodiments, the angle can be set up to another value comprised between 1 to 90 degrees. In a specific embodiment, the angle can be 15-25 degrees. Beyond 30 degrees angulation, another embodiment of the second fastener F2 with an inclinable hex tip end may be used (differential inner mechanism).

Figure 4:
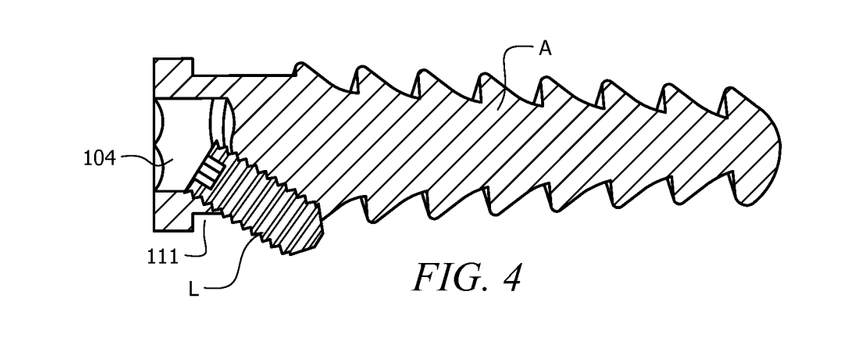
FIG. 4 is a schematic cross-sectional plan view of an anchoring member with the locking member

FIG. 4 is a schematic cross-sectional plan view of the anchoring system 100. In this representation, a headless locking member L is engaged into a oblique aperture (111) within the exemplary hex-shaped socket (104) of the head of the anchoring member A. The surface of the inner wall of the aperture may be threaded, smooth, or rough. One end of the aperture is at the proximal head of the anchor, and the opposite end is on one side of the anchor.

Figure 5:
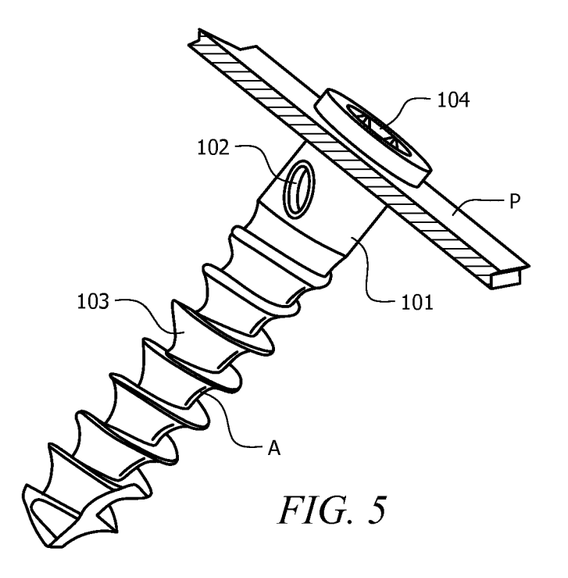
FIG. 5 is a perspective view of an anchoring member holding an object (plate).

FIG. 5 is a perspective view of an anchoring member holding an exemplary object (plate) P.

Figures 6A, 6C:
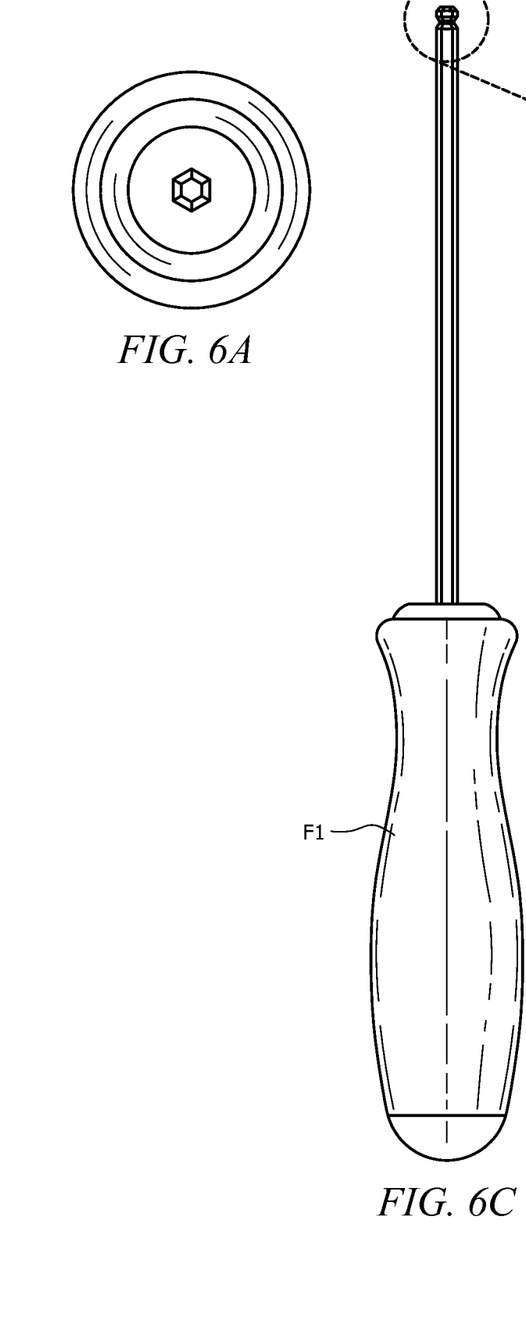
FIG. 6*a* is a cross-sectional view of the shaft (Hex Key) of one embodiment of the first fastener F1.
FIG. 6*c* is a lateral view of the first fastener F1.
Figure 6B:
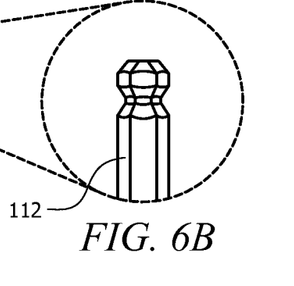
FIG. 6*b* is a schematic perspective view of the distal end (ball end hex tool) of the first fastener F1.

FIG. 6 illustrates the first fastener F1 with its Hex type tip (112). In this representation, the fastener comprises a head or tip that engages with the socket of the anchor to apply torque by rotating the tip, such as but not limited to a screwdriver, key or wrench. The tip is not limited to hex type. The second fastener F2 in certain aspects comprises a ball end hex type end to allow screwing of the locking member. The second fastener F2 can have the same features as the first fastener F1 when used in a particular embodiment e.g. with an angle α between the two members equal at 25 degrees, or inferior at 30 degrees at the maximum, in accordance with the working angle (25 to 30 degrees) of such ball end hex tip. In this case, only the size differs from the first fastener F1, the second fastener F2 being thinner than the first fastener F1 in order to be able to slid within the inner socket 104 of the first fastener F1, in particular embodiments.

Figure 7:
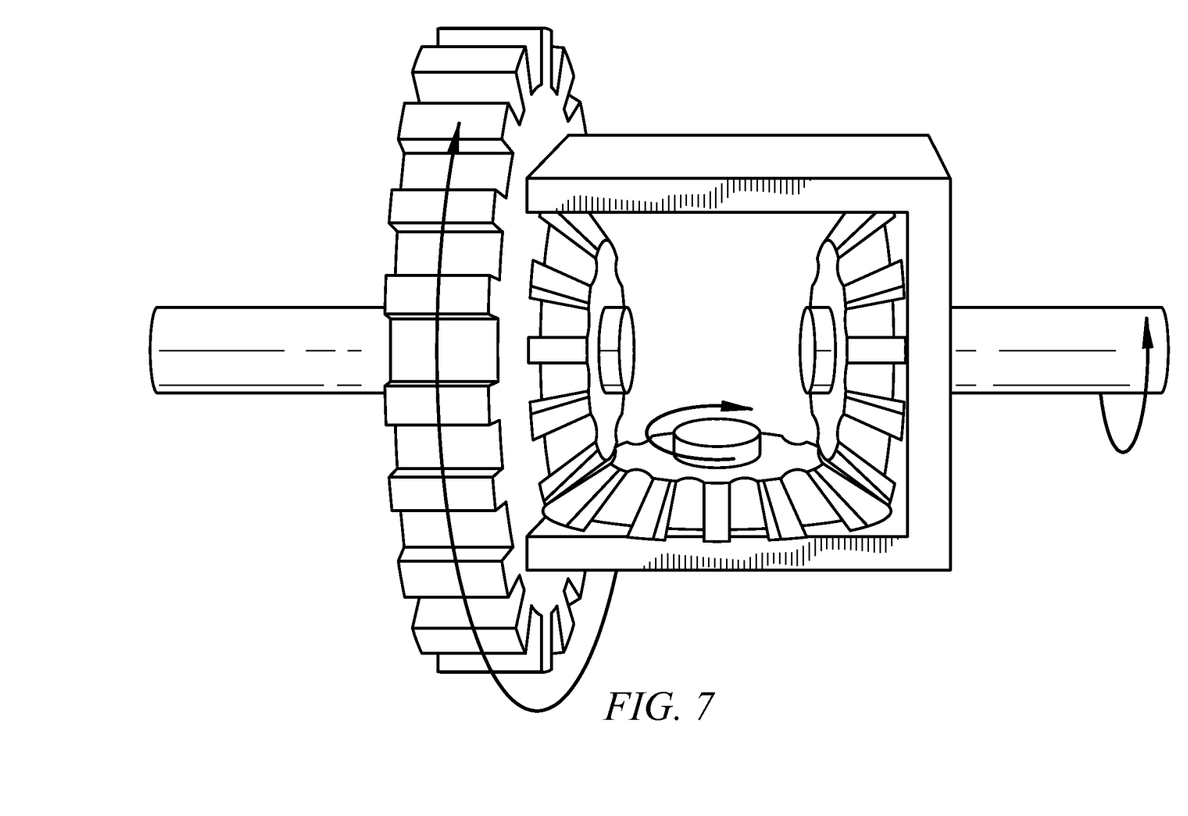
FIG. 7 is a schematic perspective view of a differential that can be used for the second fastener F2.

In another embodiment an angle β, higher than the angle α, e.g. superior at 30 degrees between the two members A and L, is set up. In this embodiment, the second fastener F2 presents an inclinable tip able to match the angle β and is equipped with an inner mechanism applying the torque in accordance with an oblique transmission of the rotating motion imparted to the handle of the fastener. Such mechanism can be but is not limited to a differential, a screw gear, or a set of gears. FIG. 7 illustrates the principle of such mechanism and shows a schematic conceptual view of a differential. Such a fastener can be rotated manually or by an electric or other motor.

Whatever the mechanism can be, it is intended to allow an oblique screwing while the handle of the fastener remains straight forward, in certain embodiments. Such a feature is useful when the local anatomical requirements forbid the tool to be tilted. For example, when a surgery using a minimally invasive approach through a small incision is performed, the instruments must go through this small cutaneous aperture, and therefore can not be angulated in order to avoid damaging soft tissue.

Figure 8A:
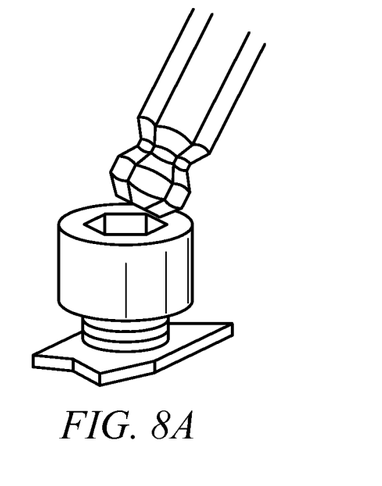
FIG. 8*a* is an enlarged perspective view of the distal end (ball end hex tool) of the first fastener F1.

FIG. 8a is an enlarged perspective view of the distal end (ball end hex tool) of the fastener. The concept by which ball ends slide into a screw head is known as funnel insertion. Basically, it means that the sides of the ball end direct (funnel) it into place. This allows fast funnel entry, eliminates wasted time even in blind applications, and the full depth engagement reduces "stripping" problems.

Figure 8B:
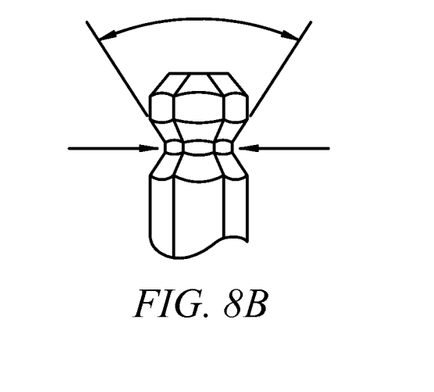
FIG. 8*b* is an enlarged lateral view of the distal end (ball end hex tool) showing a 25 to 30 degree angle entry to the hex tool.
Figure 8C:
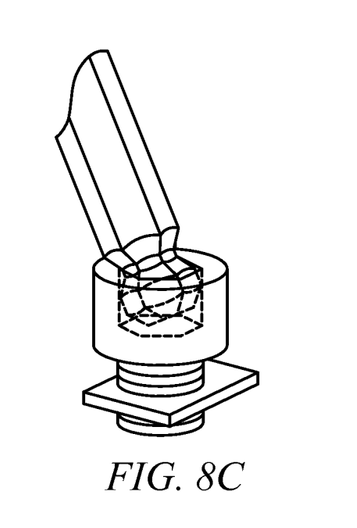
FIG. 8*c* is an example of oblique insertion.
Figure 8D:
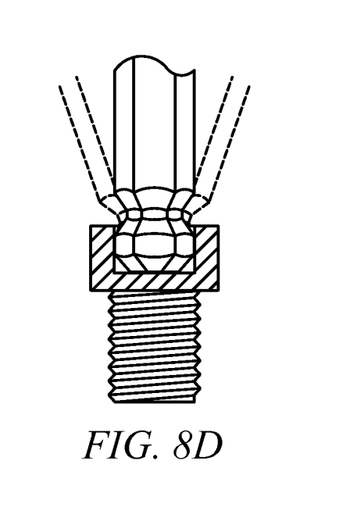
FIG. 8*d* is a lateral view of the first fastener F1 engaged within a hex screw.

FIG. 8b is an enlarged lateral view of the distal end (ball end hex tool) showing a 25 to 30 degree angle entry to hex. As maximum allowable angle increases, neck size decreases, and strength also decreases. By contrast, increasing the strength of a ball-end tool requires a corresponding increase in neck size and decrease in maximum allowable angle. Designing the perfect ball-end tool means choosing the ideal balance between strength and allowable angle. FIG. 8c is an example of oblique insertion. FIG. 8d is a lateral view of the first fastener F1 engaged within a hex screw.

Figure 9A:
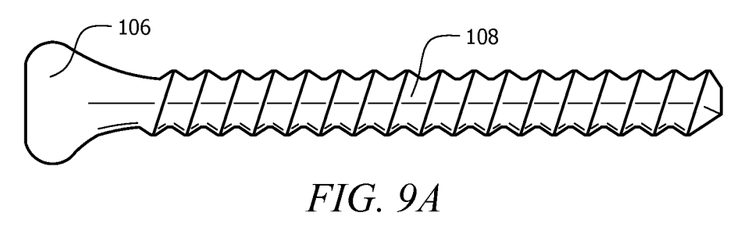
FIG. 9*a* is a lateral view of a cortical-type locking member L.
Figure 9B:
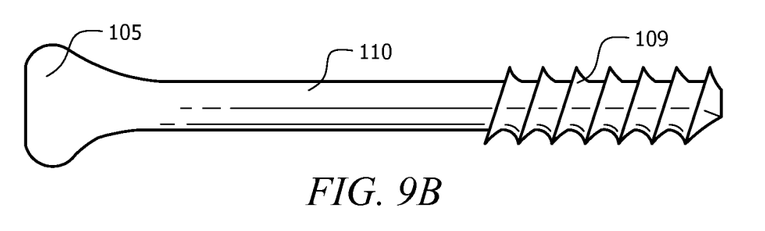
FIG. 9*b* is a lateral view of a cancelous-type locking member L.
Figure 9C:
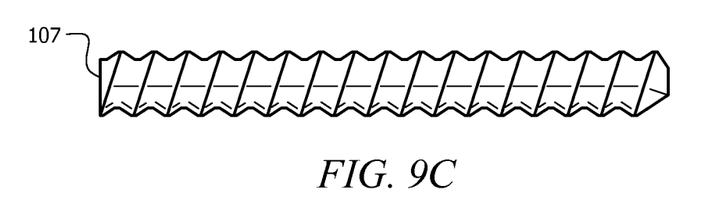
FIG. 9*c* is a lateral view of a headless-type locking member L.

FIG. 9 illustrates the three possible designs of the locking member L. In certain embodiments, the locking member L is thinner than the anchoring member A so that it can be slid through the oblique aperture and positioned within the empty room of the hexagonal socket of the anchoring member. Its length can be smaller, equal or bigger than the anchoring member. Its proximal end can be equipped with a head (105) or be wide-mouthed (106) to block within the anchoring member's head, or be headless (107). Whatever the type of the locking member L can be (headed 105, wide-mouthed 106 or headless 107), the socket has a hex type shape, in certain embodiments. The locking member can be a cortical type screw (FIG. 9a) with a fine thread (108) all along its shaft and therefore screwed into an oblique threaded canal within the anchoring member's head, or a cancelous type screw (FIG. 9b) with a coarser thread (109), designed to anchor the bone and a smooth, unthreaded portion (110), designed to slid within an oblique unthreaded canal within the anchoring member's head. Depending of its type, the locking member L can just act as an anti-rotational device and prevent the unscrewing of the anchoring member A in the cortical type design, or be both a blocking system as described above and an additional fastening device intended to secure and reinforce the grip within the medullary bone in the cancelous type design. Moreover, due to its divergent positioning, it brings to the construct a V-shaped design which opposes to pull-out forces. Whatever cancelous or cortical type design be used, the adjunction of a second divergent member (locking member L) advantageously increases both the grip and the purchase within the bone, especially in cancelous and/or osteoporotic bone and therefore opposes to pull-out and secures the fixation of any object to the bone.

Figure 10A:
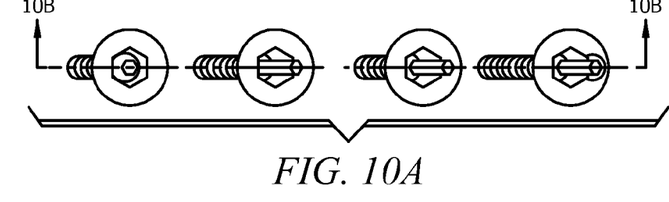
FIG. 10 illustrates various angulation patterns of the interlocking anchor and locking members.
Figure 10B:
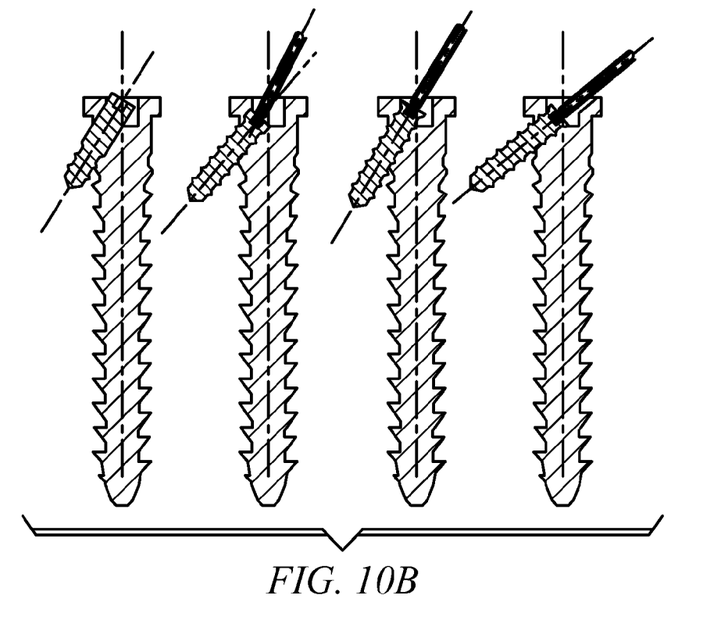
Figure 10C:
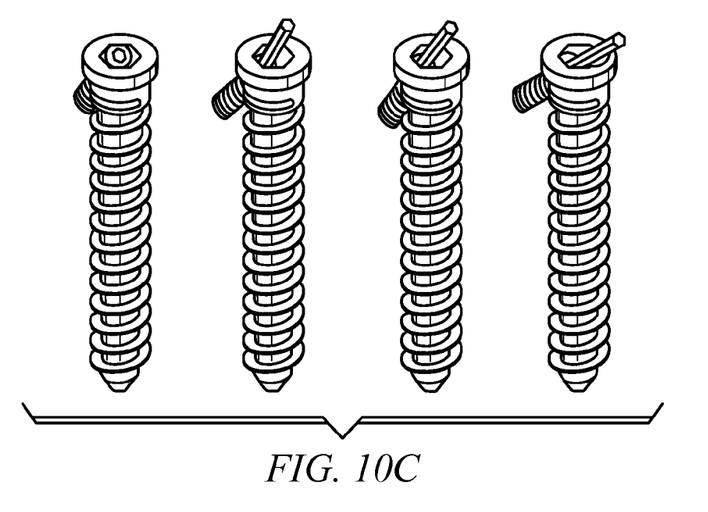

FIG. 10 illustrates various angulation patterns of the interlocking anchor and locking members. Upon certain angulations of the locking member within the anchoring member, and therefore, certain angulations required for the corresponding fastener to screw the locking member, the proximal end of the anchoring member requires a cavity at its socket to allow the fastener access to the locking member.

Figure 11:
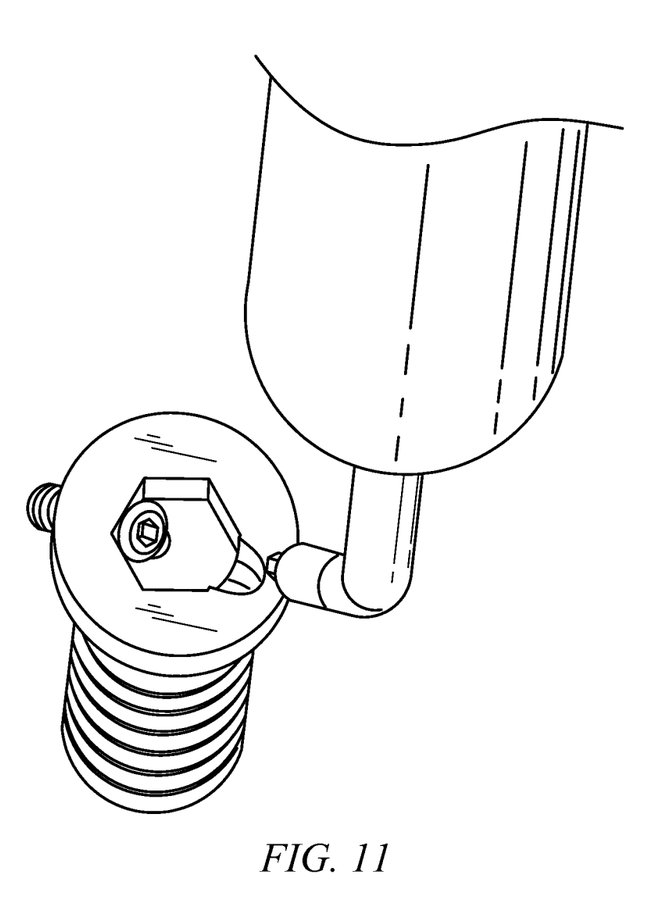
FIG. 11 illustrates one embodiment of a locking member within an anchoring member, in addition to the respective fastener having a corresponding angulation to the angulation of the locking member within the anchoring member.

FIG. 11 illustrates one embodiment of a locking member within an anchoring member, in addition to the respective fastener having a corresponding angulation to the angulation of the locking member within the anchoring member. In this specific embodiment, the proximal end of the anchoring member has a cavity that allows insertion of the fastener for the locking member.

Figure 12:
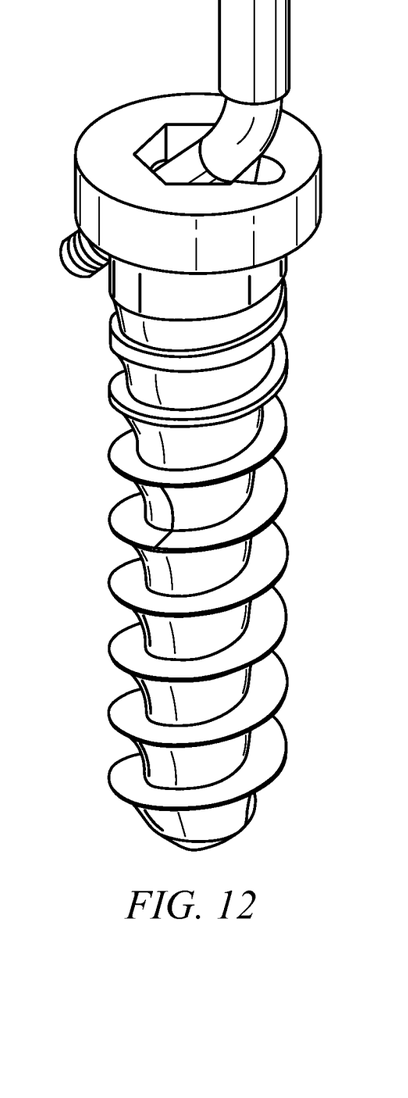
FIG. 12 illustrates an exemplary embodiment of a fastener and its corresponding locking member within the anchoring member.

FIG. 12 illustrates an exemplary embodiment of a fastener and its corresponding locking member within the anchoring member. The proximal end of the anchoring member comprises a cavity that allows insertion of the fastener for the locking member.

In certain embodiments, the anchor and locking member are coated with antibiotic or other medicine useful upon implantation of an implant on and/or in a bone. In other embodiments, the surface of the anchor and/or locking member is rough for a better grip within the bone.

Any of the compositions described herein may be comprised in a kit. Where there are more than one components in the kit, the kit also may contain a second, third or other additional container into which the additional components may be separately placed. The kits of the present invention may include a means for containing the invention component(s) in close confinement for commercial sale. Such containers may include injection or blow molded plastic containers into which the components are retained, for example.

The kit may comprise the anchor, locking member, and/or fastener(s). In some cases, all components are sold separate, whereas in other cases all or a subset of components are sold together. Irrespective of the number and/or type of containers, the kits of the invention may also comprise, and/or be packaged with, an instrument other than a fastener(s) of the invention for assisting with placing the anchor/locking member within the body of an animal.

In particular embodiments of the invention, a variety of anchors, locking members, and/or fasteners may be provided in a kit. For example, a variety of lengths, diameters, socket shapes, and/or angles of the corresponding anchors, locking members, and/or fastener(s) may be provided in a kit.

From the foregoing disclosure and detailed description of certain embodiments, it will be apparent that various modifications, additions and other alternative embodiments are possible without departing from the true scope and spirit of the invention. The embodiments discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A system configured to attach at least one object to bone tissue, comprising:
    an anchoring member configured to be driven into the bone tissue, the anchoring member having a proximal end, a distal end that is spaced from the proximal end in a distal direction along a central anchoring member axis, an outer surface spaced from the central anchoring member axis along a radial direction that is perpendicular to the central anchoring member axis, and an anchoring member socket located at the proximal end of the anchoring member, the outer surface of the anchoring member including a helical thread,
    wherein 1) the proximal end of the anchoring member includes a proximal surface that is perpendicular to the central anchoring member axis, a proximal socket opening at the proximal surface, and a socket inner wall that extends from the proximal socket opening toward the distal end along the central anchoring member axis, the proximal socket opening extending along the radial direction, and the socket inner wall defines the anchoring member socket, and 2) an aperture that extends from the socket inner wall to the outer surface of the anchoring member along a central aperture axis that is oblique relative to the central anchoring member axis, wherein the central aperture axis extends through the proximal socket opening; and a locking member defining a proximal end and a distal end, the locking member sized to be driven through the aperture along the central aperture axis until the proximal end of the locking member is seated in the aperture, whereby the distal end of the locking member extends outwardly with respect to the outer surface and is spaced from the distal end of the anchoring member along a proximal direction that is opposite the distal direction.

2. The system of claim 1, further comprising at least one tool having an end that is configured to couple to the anchoring member socket so as to transmit the torsional force to the socket inner wall.

3. The system of claim 1, wherein the locking member defines a proximal end and a distal end, such that at least a portion of the distal end is configured to extend through the aperture along the central aperture axis and into the bone tissue, and the proximal end of the locking member further defines a locking member socket.

4. The system of claim 3, wherein the locking member socket is configured to receive a tool so as to couple the tool to the locking member, thereby allowing the locking member to be driven into the bone tissue along the central aperture axis when the locking member is coupled to the tool.

5. The system of claim 3, further comprising a tool having an end that is configured to couple to the locking member socket so as to transmit torsional force to the locking member socket when the tool is coupled to the locking member socket, the end of the tool further configured to couple to the anchoring member socket so as to transmit a torsional force to the anchoring member socket when the tool is coupled to the anchoring member socket.

6. The system of claim 3, further comprising at least one tool having an end that is configured to couple to the locking member socket so as to transmit a torsional force to the locking member socket.

7. The system of claim 3, further comprising a first tool having an end that is configured to couple to the anchoring member socket so as to transmit a torsional force to the anchoring member socket, and a second tool having an end that is configured to couple to the locking member socket so as to transmit a torsional force to the locking member socket.

8. The system of claim 7, wherein the second tool includes a head and a body that is connected to the head, at least a portion of the head configured to be received in the locking member socket so as to connect the locking member to the second tool, the body is elongate along a body axis, the head is elongate along a head axis that is offset at a head angle relative to the body axis, and the head angle is substantially equal to an angle that is defined at an intersection of the central anchoring member axis and the central aperture axis.

9. The system of claim 7, wherein the second tool includes a hexagonal ball head that is configured to be received in the locking member socket.

10. The system of claim 3, wherein the locking member socket defines a shape that is hexagonal, pentagonal, square, triangular, cross-shaped, plus sign-shaped, linear, or star-shaped.

11. The system of claim 1, wherein at least one of the anchoring member and the locking member has a rough surface.

12. The system of claim 1, wherein the anchoring member includes an inner aperture wall that defines a surface that, in turn, defines the aperture, and the surface is smooth, rough, or threaded.

13. The system of claim 1, wherein the central anchoring member axis extends at an angle with respect to the central aperture axis, and the angle is between 1 and 89 degrees.

14. The system of claim 13, wherein the angle is between 10 and 75 degrees.

15. The system of claim 14, wherein the angle is between 10 and 50 degrees.

16. The system of claim 15, wherein the angle is between 10 and 35 degrees.

17. The system of claim 16, wherein the angle is between 25 and 30 degrees.

18. The system of claim 1, wherein the anchoring member socket defines a shape that is hexagonal, pentagonal, square, triangular, cross-shaped, plus sign-shaped, linear, or star-shaped.

19. The system of claim 1, wherein the anchoring member socket is configured to receive a tool so as to couple the tool to the locking member, thereby allowing the locking member to be driven into the bone tissue along the central aperture axis when the locking member is coupled to the tool.

20. The system of claim 1, wherein the distal end of the anchoring member is threaded, and the distal end of the locking member is threaded.

21. The system of claim 1, wherein the proximal end of the anchoring member is unthreaded.

22. The system of claim 1, wherein the socket defines a distal socket end spaced from the proximal socket opening along the central anchoring member axis, the inner wall extends from the socket opening to the distal socket end.

23. The system of claim 1, wherein when the proximal end of the locking member is seated in the aperture, the distal end of the locking member is further spaced from the distal end of the anchoring member along the radial direction.

24. A system configured to attach at least one object to bone tissue, comprising:

an anchoring member having an anchoring member body that defines a proximal end and a distal end that is spaced from the proximal end in a distal direction along a central anchoring member axis, the proximal end of the anchoring member defining an anchoring member socket that extends into the anchoring member body along the distal direction, and the anchoring member defines an aperture that extends through the anchoring member body, the anchoring member including a helical thread that extends around an entirety of an outer surface of the anchoring member body, wherein 1) the anchoring member body has a proximal surface that defines an opening of the anchoring member socket, the opening extending along a radial direction that is transverse to the central anchoring member axis, and a socket inner wall that extends from the proximal surface toward the distal end so as to partially define the anchoring member socket, and 2) the aperture extends along a central aperture axis that is oblique to the central anchoring member axis and to the proximal surface, the central aperture axis extending through the proximal socket opening, the anchoring member including an aperture proximal end disposed at the socket inner wall and an aperture distal end that is spaced from the aperture proximal end along the central aperture axis in the distal direction, such that, the aperture distal end is spaced from the distal end a distance that is greater than a distance that the aperture proximal end is spaced from the proximal end.

25. The system of claim 24, wherein the anchoring member body further defines an outer surface that is spaced from the central anchoring member axis along the radial direction, and the aperture distal end is disposed at the outer surface.

26. The system of claim 24, further comprising a locking member, at least a portion of the locking member configured to be inserted through the socket and further through the aperture so as to extend into the bone tissue.

27. The system of claim 26, wherein the distal end of the anchoring member body is threaded, and at least a portion of the locking member is threaded.

28. The system of claim 27, wherein the proximal end of the anchoring member body is unthreaded.

29. The system of claim 24, further comprising at least one tool that is configured to fit in the anchoring member socket so as to transmit a torsional force to the anchoring member, and at least one tool that is configured to couple to the locking member socket so as to transmit a torsional force to the locking member.

30. The system of claim 29, wherein the at least one tool is configured to fit in the anchoring member socket and couple to the locking member socket.

31. A system configured to attach at least one object to bone tissue, the system comprising:
   a bone screw having a bone screw body that defines a proximal end and a distal end that is spaced from the proximal end along a central bone screw axis in a distal direction, wherein the proximal end defines an anchoring member socket that extends into the bone screw, and the bone screw defines an aperture that extends through the bone screw body along a central aperture axis; and
   a locking member having at least a portion that is configured to be inserted through the aperture and into the bone tissue after the bone screw has been driven into the bone tissue;
   wherein 1) the bone screw socket defines a socket opening disposed at a proximal-most end of the bone screw, the socket opening extending along a radial direction that is angularly offset to both the central anchoring member axis and the central aperture axis, the bone screw socket extends from the socket opening into the bone screw body along the central bone screw axis, and 2) the aperture includes first and second opposed terminal ends spaced from each other, the first terminal end open to the socket so as to receive the locking member when the locking member is inserted through the socket opening and along central aperture axis, the second terminal end extending out the bone screw body, the second terminal end being spaced from the first terminal end along the central anchoring member axis in the distal direction, such that the second terminal end is closer to the proximal end of the bone screw than the distal end of the bone screw,
   wherein an entirety of the aperture is spaced from an entirety of the proximal-most end of the bone screw in the distal direction.

32. The system of claim 31, wherein the central aperture axis is oblique with respect to the central bone screw axis.

33. The system of claim 31, wherein the distal end of the bone screw body is threaded, and at least a portion of the locking member is threaded.

34. The system of claim 33, wherein the proximal end of the bone screw body is unthreaded.

35. The system of claim 31, wherein the proximal-most end defines a proximal surface and the proximal opening is aligned with the proximal surface.

36. A system configured to attach at least one bone screw to bone tissue, comprising:
   a bone screw defining a proximal end, a distal end spaced from the proximal end along a central screw axis, and an outer surface spaced from the central screw axis along a radial direction that is perpendicular to the central screw axis,
   the bone screw comprising a socket that is located at the proximal end of the bone screw and extends toward the distal end along the central screw axis, the socket defined by a socket inner wall that is spaced from the outer surface along the radial direction, wherein the socket inner wall is unthreaded,
   the bone screw including an aperture having an aperture proximal end located at the socket inner wall and an aperture distal end located at the outer surface, the aperture elongate along a central aperture axis that is oblique to the central screw axis, the aperture distal end being spaced from the proximal end of the bone screw a distance that is greater than a distance that the aperture proximal end is spaced from the proximal end of the bone screw, wherein the aperture proximal end is spaced from an entirety of the proximal end of the bone screw in the distal direction;
   a tool that is configured to fit in the socket so as to transmit a torsional force to the socket inner wall that drives the bone screw to rotate about the central screw axis; and
   a locking member having a head and a shaft that extends from head,
   wherein the socket is configured to receive the locking member such that at least a portion of the shaft is configured to be inserted through the socket and the aperture proximal end along the central aperture axis into the bone tissue after the anchoring member has been driven into the bone tissue.

37. The system of claim 36, wherein the bone screw is at least partially threaded with a thread that extends around the entirety of the bone screw.

38. The system of claim 36, wherein the locking member is a locking screw, and the locking screw is at least partially threaded.

39. The system of claim 36, wherein the head of the locking member is configured to be retained in the socket.

40. The system of claim 39, wherein the locking member defines a proximal end and a distal end spaced from the proximal end along a locking member axis, the locking member head located at the proximal end, and a locking member socket disposed at the head of the locking member.

41. The system of claim 40, wherein the tool is a first tool, and wherein the system further comprises a second tool includes a second tool head and a tool body that is connected to the head, at least a portion of the second tool head configured to be received in the locking member socket so as to connect the locking member to the second tool, the tool body is elongate along a tool body axis, the second tool head is elongate along a head axis that is offset at a head angle relative to the tool body axis, and the head angle is substantially equal to an angle that is defined by the intersection of the central screw axis and the central aperture axis.

42. The system of claim 36, wherein the proximal end of the bone screw defines a proximal surface and a proximal opening that is aligned with the proximal surface, wherein the socket extends from the proximal surface toward the distal end of the bone screw along the central screw axis.

43. The system of claim 42, wherein the socket includes a distal socket end spaced from the proximal surface along the central screw axis, and the socket inner wall extends from the proximal surface to the distal socket end, wherein a distance between the aperture proximal end and the distal socket end is less than then a distance between the proximal surface and the aperture proximal end.

* * * * *